United States Patent [19]

Myers

[11] 4,054,133
[45] Oct. 18, 1977

[54] CONTROL FOR A DEMAND CANNULA

[75] Inventor: William P. Myers, Davenport, Iowa

[73] Assignee: The Bendix Corporation, South Bend, Ind.

[21] Appl. No.: 671,195

[22] Filed: Mar. 29, 1976

[51] Int. Cl.² .......................................... A61M 16/00
[52] U.S. Cl. .................................. 128/142.2; 128/206
[58] Field of Search ........... 128/142.2, 142 R, 140 N, 128/145.5, 145.6, 145.8, 147, 203, 188, DIG. 17, DIG. 29; 251/282, 61.1; 137/599

[56] References Cited

U.S. PATENT DOCUMENTS

| 1,309,686 | 7/1919 | Heidbrink | 128/203 |
|---|---|---|---|
| 2,121,311 | 6/1938 | Anderson et al. | 128/145.8 |
| 3,043,302 | 7/1962 | Spears et al. | 128/203 |
| 3,114,365 | 12/1963 | Franz | 128/145.8 |
| 3,333,581 | 8/1967 | Robinson et al. | 128/145.6 |
| 3,400,713 | 10/1968 | Finan | 128/203 |
| 3,434,471 | 3/1969 | Liston | 128/145.8 |
| 3,797,803 | 3/1974 | Goto et al. | 251/282 |
| 3,830,257 | 8/1974 | Metivier | 128/145.8 |
| 3,853,105 | 12/1974 | Kenagy | 128/145.8 |
| 3,913,576 | 10/1975 | Martin et al. | 128/142.2 |

Primary Examiner—Robert W. Michell
Assistant Examiner—Henry J. Recla
Attorney, Agent, or Firm—Leo H. McCormick, Jr.; Ken C. Decker

[57] ABSTRACT

A control for regulating the flow of a breathable fluid from a storage container to a recipient as a function of the differential between inhalation and exhalation pressure measured in the nasal cavity.

13 Claims, 3 Drawing Figures

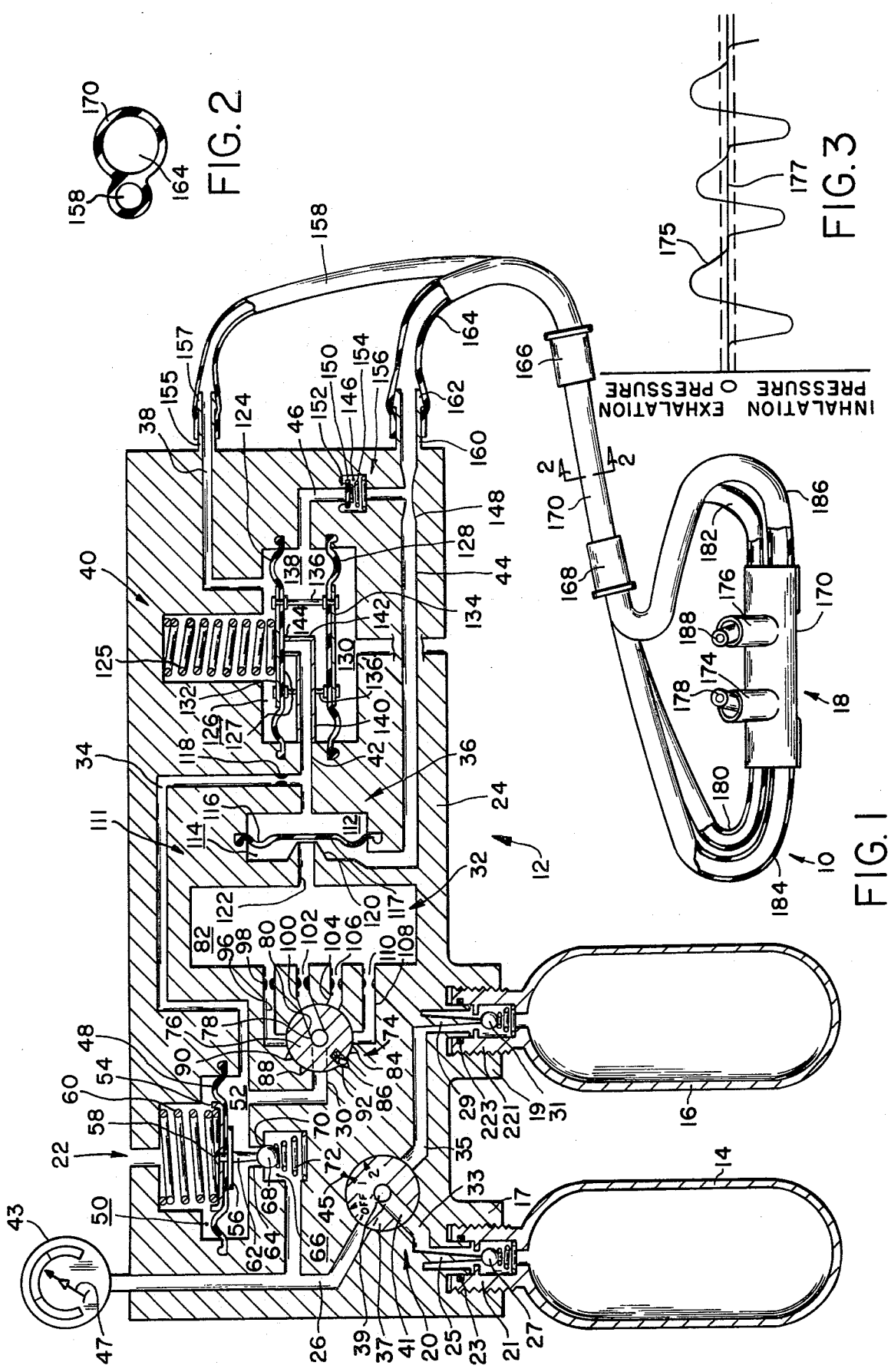

CONTROL FOR A DEMAND CANNULA

BACKGROUND OF THE INVENTION

Recent developments in medicine have shown that the effects of respiratory aliments and post operative convalescence can be reduced through the continual administration of oxygen to a patient.

Most often the administration of oxygen to the patient is achieved through the use of some type of oxygen mask. Unfortunately, most oxygen masks are cumbersome and require a seal to be formed with the face of each patient. Without such a seal, a desired oxygen flow cannot be achieved.

The need of a face seal was elminated by the use of nasal cannulas such as disclosed in U.S. Pat. No. 3,915,173. In this device, a tube inserted in the nasal cavity has bulbular sections for sealing the oro-pharyngeal and the endotracheal areas from the atmosphere to directly supply the lungs with a breathable oxygen enriched fluid. As long as the patient is under the influence of anesthesia, this post operative cannula device is satisfactory. However, when the patient awakes, the tube causes an interference which hampers talking since exhalation gases are expelled through a constant flow valve in the supply conduit and not through the mouth. Thus, when the patient is revived, a standard cannula, such as disclosed in U.S. Pat. No. 3,802,431 is utilized to supply the needed oxygen enriched breathable fluid. With this cannula, the patient can eat and talk without discomfort. However, with all these cannulas, a constant flow of oxygen at the maximum usage rate is always necessary to assure proper respiratory medication.

Constant flow of the breathable fluid results in considerable loss of oxygen since a patient is normally inhaling only approximately 40% of the time while the remaining oxygen flow is lost to the atmosphere without helping the patient. In order to conserve oxygen, a control means as taught in U.S. Pat. No. 3,400,713, was devised. This control means has a belt which surrounds the waist of the patient and with each inhalation and exhalation, expansion and contraction of the lungs allows a resilient means to operate a valve which opens and shuts the communication of the supply port connected to the oxygen supply. Medical investigations have found the most beneficial use of oxygen occurs during the initial portion of the inhalation period. Unfortunately, the delay between the movement of the chest of the patient and the operation of the valve results in a corresponding delay in the communication of oxygen enriched breathable fluid into the lungs.

SUMMARY OF THE INVENTION

While searching for a means to provide a patient with a more efficient use of oxygen, I discovered that pressure present in the nasal cavity could be sensed to indicate when a patient was inhaling and exhaling. During each breathing cycle, I was able to measure the following three distinct phases: inhalation, pause and exhalation. Thereafter, I devised a control means responsive to those three distinct phases for use with a cannula to regulate the flow of oxygen from a supply chamber.

The control means has a housing with a plenum which retains a fixed quantity of oxygen enriched breathable fluid. The plenum has an orifice connected by a passageway through which the oxygen enriched breathable fluid is communicated to the nasal cavity. A wall means separates the orifice from a control chamber. An operational pressure holds the wall means against the orifice to seal the plenum. A sensor has a first chamber connected to the nasal cavity, a second chamber connected to the atmosphere and a fixed volume chamber connected to the control chamber. When the inhalation phase in the breathing cycle of the patient starts, a pressure differential occurs between the first chamber and the second chamber. This pressure differential moves the sensor and allows an operational pressure in the control chamber to be communicated into the constant volume chamber. Communication of the operational pressure into the constant volume chamber allows the wall means to move away from the orifice. Thereafter, the fixed quantity of oxygen enriched fluid in the plenum is communicated through the passageway to the nasal passageway and presented to the recipient during the inhalation phase of the breathing cycle.

It is the object of this invention to provide a breathing system with a control means for use with a cannula located in the nasal passages of a patient. The control means responds to a sensed pressure differential between inhalation and exhalation pressure in the nasal passages for the development of an operational signal. The operational signal allows a fixed quantity of oxygen enriched breathable fluid to be presented to the patient at the start of an inhalation phase of a breathing cycle.

It is another object of this invention to provide a breathing system with a demand cannula having a distribution section and a sensing section whereby the nasal cavity pressure during exhalation phase activates a valve to only allow oxygen enriched breathable fluid to be supplied to a patient during an inhalation phase of a breathing cycle.

It is another object of this invention to provide a control means which senses inhalation and exhalation pressures in a nasal cavity of a recipient to control the flow of an oxygen enriched breathable fluid.

It is a further object of this invention to provide a supply passageway in a breathing system with a venturi section for aspirating a control fluid from a control chamber in a control means to prevent a pressure build up in the control chamber until completion of an inhalation phase of a breathing cycle of a recipient.

These and other objects will become apparent from reading this specification and viewing the drawings.

BRIEF DESCRIPTION OF THE DRAWINGS

FIG. 1 is a schematic illustration of a breathing system showing a sectional view of a control means constructed according to the principles of this invention for regulating the flow of an oxygen enriched breathable fluid supplied to a recipient;

FIG. 2 is a sectional view of a distribution conduit for the breathing system taken along line 2—2 of FIG. 1; and FIG. 3 is a graph showing a typical pressure pattern measured in the nasal passage of a recipient during a breathing cycle.

DETAILED DESCRIPTION OF THE PREFERRED EMBODIMENT

The breathing system 10, shown in FIG. 1, has a control means 12 for regulating the communication of breathable fluid from either storage container 14 or 16 through a cannula means 18 to a recipient.

The control means 12 has a housing 24 with a supply passageway 26, which connects an operational switch means 20 with regulator means 22; a distribution passageway 30, which connects the regulator means 22 with plenum means 32; a control passageway 34, which connects the regulator means 22 with a wall means 36; a sensor passageway 38, which connects a sensor means 40 with the cannula means 18; a relief passageway 42, which connects the wall means 36 with the sensor means 40; an outlet passageway 44, which connects the plenum means 32 with the cannula means 18; and an aspirator passageway 46, which connects the sensor means 40 with the outlet passageway 44. Through the interconnection of the above recited passageways, the entire amount of breathable fluid released from storage containers 14 and 16, even that utilized as a control parameter, is supplied to the recipient through the cannula means 18.

In more particular detail, the housing 24 has a first entrance port 17 and a second entrance port 19 having threads thereon for attaching the first and second supply or storage containers 14 and 16 to the control means 12. Each of the supply containers 14 and 16 have necks 21 and 221 on which O-ring seals 23 and 223 are located to engage the housing 24 and form a fluid tight seal. First and second pintles 25 and 29 extend from the housing 24 to engage balls 27 and 31 in the necks 21 and 221 of storage or supply containers 14 and 16 to allow communication of the breathable fluid therein to flow into first and second branches 33 and 35 of the supply passageway 26.

The operational switch means 20 has a cylindrical body 37. The cylindrical body 37 has axial passageway 39 connected to supply conduit 26 and a radial passageway 41. The radial passageway 41 is adapted to be connected to the first and second branches 33 and 35. The cylindrical body 37 has indicator indicia (OFF, 1,2) located thereon for informing the operator of the supply container which is connected to the supply conduit 26.

In addition, a gage 43 is also connected to the supply conduit 26 to inform the operator of the approximate quantity of oxygen enriched breathable fluid in the operational supply container. In some fields of use, a low volume alarm is connected to the supply conduit 26 to warn the operator that the supply is reaching a low level and a change from one supply container to the other may be desirable. The supply conduit 26 terminates in a high pressure chamber 66 adjacent the regulator means 22. Communication from the high pressure chamber 66 through bore 64 is entirely controlled by the regulator means 22.

The regulator means 22 has a diaphragm 48 which divides a cavity in the housing 24 into an atmospheric chamber 50 and a flow-through-chamber 52. A spring retainer 54, located in the atmospheric chamber 50, is connected to a plate 56, in the flow-through-chamber 52, by a rivet 58. The center portion of the diaphragm 48 is sandwiched between the spring retainer 54, and the plate 56, by the rivet 58. The plate 56 has a projection 62 which extends into bore 64. A ball 68 located in the high pressure chamber 66 is urged toward seat 70 associated with bore 64 by spring 72 to prevent communication between the high pressure chamber 66 and the flow-through-chamber 52. A spring 60, caged between the retainer 54 and the housing 24, urges projection 62 toward the ball 68. When the pressure differential across the diaphragm 48, between air in the atmospheric chamber 50 and the breathable fluid in the flow-through-chamber 52, is below a predetermined value, typically 10 psig, spring 60 moves the diaphragm 48 toward the flow-through-chamber 52 causing the projection 62 to unseat ball 68 from seat 70 and allows communication of the breathable fluid from the high pressure chamber 66. When a sufficient amount of breathable fluid has passed between the high pressure chamber 66 and the flow-through-chamber 52 to alleviate the pressure differential, the diaphragm 48 moves toward the atmospheric chamber and allows spring 72 to urge ball 68 toward seat 70 and thereby interrupt the communication of breathable fluid through bore 64.

The distribution passage 30 connects the flow-through-chamber 52 to a selector valve means 74 which is associated with the plenum means 32. The selector valve means 74 has a cylindrical body 76. The cylindrical body 76 has an axial bore 78 connected to the distribution passageway 30 and a radial bore 80 for distribution of the oxygen enriched breathable fluid into the storage chamber 82 of the plenum means 32. The housing 24 has a series of detents 84, 86, 88 and 90 adjacent the cylindrical body 76. A ball 92 in the cylindrical body 76 is biased into a selected detent 84, 86, 88 or 90 to prevent the cylindrical body 76 from rotating after an operator has selected a desired flow rate from the flow-through-chamber 52.

The housing 24 has a first passage 96 with a first orifice 98, a second passage 100 with a second orifice 102, a third passage 104 with a third orifice 106, and a fourth passage 108 with a fourth orifice 110 through which the radial bore 80 of the selector valve means 74 is connected with the storage chamber 82. The orifices 98, 102, 106 and 110 are circular. The size of each orifice will vary from each other as square of the radius in accordance with the following formula:

$$Q = VA$$

where:
$Q$ = Quantity of fluid in liters/min.
$V$ = Velocity of the fluid
$A$ = Area of the fluid Since the orifices 98, 102, 106 and 110 are all circular, A can be written as follows $\pi \bar{r}^2$. Thereafter the quantity equation $Q$ can be written as follows:

$$Q = V\pi \bar{r}^2$$

From this equation, it can be shown that the flow rate into the storage chamber 82 of the plenum means 32 is directly related to the radius of the orifice to which the radial bore 80 is connected. Since the storage chamber 82 retains a fixed quantity of the oxygen enriched breathable fluid for each flow rate selected, the communication of oxygen enriched breathable fluid from the storage chamber 82 is regulated by a first wall means 36 of a control means 111.

The control means 111 has first wall means 36 with a diaphragm 116. The diaphragm 116 divides a cavity in the housing 24 into a control chamber 112 and a distribution chamber 114. Control passageway 34 connects control chamber 112 with the flow-through-chamber 52. An orifice 118 controls the flow rate of the oxygen enriched breathable fluid present in the control passageway 34 into the control chamber 112.

The housing 24 has a passage 122 which connects the storage chamber 82 with the distribution chamber 114. An annular projection 120 surrounds the passage 122 to provide a seat for diaphragm 116. The diaphragm 116 engages projection 120 to prevent flow of the oxygen enriched breathable fluid from storage chamber 82 into the distribution chamber 114 during the exhalation phase of the breathing cycle of a recipient.

The distribution chamber 114 is directly connected to the outlet passage 44 for communicating the oxygen enriched breathable fluid in the storage chamber 82 to the recipient upon movement of the wall means 36 away from passage 122.

The operation of the wall means 36 is controlled by sensor means 40. Sensor means 40 responds to the inhalation and exhalation phases in a breathing cycle of a recipient. The sensor means 40 has a first diaphragm 124, which is attached to the housing 24 to establish a sensing chamber 126, and a second diaphragm 128 which is attached to the housing 24 to establish an atmospheric chamber 130. A first backing plate 132 is attached to the first diaphragm 124 and a second backing plate 134 is attached to the second diaphragm 128. A series of struts or linkage means 136' attached to the first backing plate 132 and the second backing plate 134 establishes a constant volume relief chamber 138 between the first diaphragm 124 and the second diaphragm 128 within the housing 24. A conduit 140 is attached to the housing 24 for extending the relief passageway 42 into the center of the constant volume relief chamber 138. The conduit 140 has an end section 142 with a face 144 parallel to the center surface of the first diaphragm 124. A spring 125 acts on the first backing plate 132 to move the face 127 against the face 144 of the conduit extension 142 to separate the constant volume relief chamber 138 from relief passageway 42. The constant volume relief chamber 138 is connected to the output passageway 44 through relief passageway 46.

The relief passageway 46 has a relief chamber 146 located therein adjacent a venturi section 148 in the outlet passageway 44.

A check valve means 156 is located in the relief chamber 146. The check valve means 156 has a disc 150 which is urged toward seat 152 by a spring 154. The spring 154 has sufficient resiliency to move the disc 150 onto seat 152 during an exhalation phase while allowing substantially free flow during the inhalation phase of a breathing cycle.

The housing 24 has a first nipple 155 with an annular shoulder 157 located thereon for attaching a sensing conduit 158 to the sensing passageway 38 and a second nipple 160 with an annular shoulder 162 located thereon for attaching a distribution conduit 164 to the outlet passageway 44.

A first coupling 166 joins the individual sensing conduit 158 and distribution 164 into a single structure conduit 170 as shown in FIG. 2. The length of the single structure conduit 170 can be varied to meet the needs of the recipient.

A second coupling 168 divides the sensing conduit 158, into a first branch 180 and a second branch 182, and the distribution conduit 164 into a first branch 184 and a second branch 186.

The first branch 184 of the distribution conduit 164 is connected to a first tubular radial projection 174 extending from the cylindrical body 170 of the cannula means 18. The first branch 180 of the sensing conduit 158 has an extension 178 which is located in the first tubular radial projection 174.

Similarly, the second branch 186 of the distribution conduit 164 is connected to a second radial projection 176 extending from the cylindrical body 170 of the cannula means 18. The second branch 182 of the sensing conduit 158 has an extension 188 which is located in the second tubular radial projection 176.

The first and second tubular radial projections 174 and 176 are adapted to be inserted into the nasal cavity of the recipient.

MODE OF OPERATION OF THE PREFERRED EMBODIMENT

When a recipient is in need of oxygen enriched breathable fluid, an operator moves switch means 20 to an ON position, as shown in FIG. 1, to a position where indicia 1 is aligned with arrow 45. Breathable fluid in storage container 14 can now flow into the first branch 33, through radial passageway 41, and into the axial passageway 39 for communication into the supply conduit 26. Pointer 47 on gage 43 indicates the quantity of the breathable fluid in the storage container 14. If the quantity of breathable fluid in the storage container 14 is below a predetermined value, the operator moves the cylindrical body to a second position where indicia 2 is aligned with arrow 45 to allow communication of breathable fluid from the second container 16.

The high pressure oxygen enriched breathable fluid in the supply conduit 26 is communicated into the high pressure chamber 66. Initially, spring 60 moves ball 68 away from seat 70 and allows the high pressure breathable fluid to enter the flow-through-chamber 52. However, as the pressure in the flow-through-chamber rises to approximately 10 psig, the pressure acting on diaphragm overcomes the spring 60 and moves the projection 62 out of engagement with ball 68. Thereafter, spring 72 urges ball 68 against seat 70 to seal the high pressure chamber 66.

The oxygen enriched breathable fluid located in the flow-through-chamber 52 is simultaneously communicated through distribution passageway 30 going to the selector valve means 74 and through control passageway 34 going to the first wall means 36 of the control means 111. Thereafter, the operator, depending upon the recipient's need for oxygen enriched breathable fluid, moves the cylindrical body 76 to align radial passage 80 with the appropriate flow passage, shown in FIG. 1 as passage 100. The oxygen enriched breathable fluid continually flows from the distribution passage 30, through axial passage 78, out the radial passage 80, past orifice 102 and into the storage chamber 82. At the same time, oxygen enriched breathable fluid flows in control passageway 34, through orifice 118 and into control chamber 112. The oxygen enriched breathable fluid acts on diaphragm 116 to move face 117 against face 120 and seal passage 122. With passage 122 sealed, a fixed quantity of breathable fluid is retained in storage chamber 82.

Initially, the pressure in the sensing chamber 126 and the atmospheric chamber 130 is the same. Spring 125 acts on the first backing plate 132 to prevent communication between the relief passageway 42 and the constant volume relief chamber 138.

When the control valve means 12 stabilizes, as indicated by an absence of the flow of oxygen enriched breathable fluid from the first and second tubular projections 174 and 176, the cannula means 18 can be connected to the recipient.

The first and second tubular projections 174 and 176, are inserted in the nasal cavities of the recipient. As the recipient breathes, a pressure pattern 175 as indicated in FIG. 3 is sensed.

During each inhalation phase of a breathing cycle, a negative pressure, shown below base line 177, occurs in the nasal cavity. This negative pressure as sensed by extensions 178 and 188 of the sensing conduit 158 is communicated into sensing chamber 126. With a negative or pressure below atmospheric pressure in the sensing chamber 126, and a positive or pressure at atmospheric pressure in the atmospheric chamber 130, a pressure differential occurs across the first and second diaphragms 124 and 128 which overcomes spring 125. This pressure differential moves the face 127 of the first diaphragm 124 away from the end 144 of the relief passage extension 140 to allow the pressurized of the oxygen enriched breathable fluid in the control chamber 112 to flow into the constant volume chamber 138. With the release of the oxygen enriched breathable fluid from the control chamber 112, the pressurized of the oxygen enriched breathable fluid in storage chamber 82 moves face 117 away from seat 122. The oxygen enriched breathable fluid flows in the outlet passage 44, past venturi 148 and into the distribution conduit 164 for delivery through the first and second branches 184 and 186 to the recipient.

When oxygen enriched breathable fluid flows through the venturi section 148, a pressure differential develops across disc 150 of the check valve means 156. This pressure differential moves disc 150 away from seat 152 to aspirate, or draw, the oxygen enriched breathable fluid communicated into the constant volume relief chamber 138 through the relief passage 42, and into the distribution conduit 164. During the inhalation phase of the breathing cycle, after the dumping of the fixed volume of breathable fluid from the storage chamber 82, flow through the distribtion conduit 30 continues at a rate determined by the orifice size selected by the operator on the selector valve means 74. As the pressure in the flow-through-chamber 52 drops below a preselected value, typically about 10 psig, spring 60 moves the diaphragm 48 toward the flow-through-chamber 52 and brings projection 64 into engagement with ball 68. Further movement of the diaphragm 48 causes the projection 64 to move ball 68 away from seat 70 and allows high pressure oxygen enriched breathable fluid to enter into and raise the pressure in the flow-through-chamber 52. When the pressure in the flow-through-chamber 52 reaches the preselected value, spring 60 is overcome, and projection 62 moves away from ball 68. With the projection 62 out of engagement with ball 68, spring 72 seats the ball 68 on seat 70 and interrupts the communication between the high pressure chamber 66 and the flow-through-chamber 52. This type of modulation automatically occurs whenever the pressure in the flow-through-chamber 52 drops below the preselected value.

At the end of the inhalation phase in the breathing cycle, a positive pressure, shown in FIG. 3 as above line 177, occurs in the exhalation phase of the breathing cycle. This positive pressure is communicated to the sensing chamber 126 to eliminate the pressure differential across the first and second diaphragms 124 and 128. The elimination of the pressure differential allows spring 125 to move face 127 into engagement with face 144 of the conduit extension 140 and terminate communication between the control chamber 112 and the constant volume chamber 138. With the relief passage extension 140 sealed oxygen enriched breathable fluid present in the control passageway 34 is directed into the control chamber 112. With oxygen enriched breathable fluid in the control chamber 112, the pressure acts on diaphragm 116 to move face 117 against seat 120. With face 117 seated on seat 120, the flow of the oxygen enriched breathable fluid into the storage chamber 82 continues until a fixed volume of breathable fluid at a predetermined pressure is retained.

At the termination of the exhalation phase, a slight pause occurs in the breathing cycle of human beings. During this pause segment, the pressure in the sensing chamber 126 approaches the pressure in chamber 130. Thereafter, the inhalation phase of the next breathing cycle begins and a negative pressure transmitted to the sensing chamber 126 again creates the operational pressure differential. The operational pressure differential controls the position of the diaphragm 116 of the wall means 36. When the wall means 36 moves, the fixed volume of oxygen enriched breathable fluid is immediately communicated to the recipient through the outlet passage 44 and supply conduit 164. This cycle is repeated in each breathing cycle as long as the oxygen enriched breathable fluid is available in the supply containers 14 and 16.

I claim:

1. A control means for regulating the communication of pressurized breathable fluid from a storage container to a recipient, comprising:

a housing having a plenum chamber, a distribution chamber, a control chamber, a sensing chamber, a relief chamber, a first outlet port and a second outlet port, said plenum chamber being connected to a storage container of pressurized breathable fluid through a first passageway, said control chamber being connected directly to said first passageway through a control passage, said sensing chamber being connected to said first outlet port by a second passageway, said distribution chamber being connected to said plenum chamber through a distribution passage and to said second outlet port through a third passageway, said control chamber being connected to said relief chamber through a relief passage, said relief chamber including means for relieving pressure accumulated therein, said housing having a plurality of orifices varied flow rate located in said first passageway downstream of the connection between said control passage and said first passageway for connecting the storage container with said plenum chamber;

means adapted for connection to the nasal passages of a recipient;

a first conduit connected to said first outlet port at one end and to said means adapted for connection to the nasal passages of the recipient;

a second conduit connected to said second outlet port at one end and to said means adapted for connection to the nasal passages of the recipient at the other end;

actuator means connected to the first passageway for permitting said pressurized breathable fluid to flow from the storage container into said first passageway;

selector means for choosing a flow rate orifice from said plurality of orifices which allows continual communication of a fixed quantity of breathable fluid from said first passageway into the plenum means corresponding to the metabolic needs of a recipient;

first wall means located in said housing for separating said control chamber from said distribution chamber and for controlling flow of fluid from said distribution chamber through said distributor passage; and second wall means located in said housing for separating said sensing chamber from said relief passage for controlling flow from said relief passage, said second wall means responding to an exhalation pressure communicated from the nasal passages through said first conduit to said sensing chamber to seal said relief passage causing the pressurized breathable fluid in the control passage to flow into said control chamber and urge said first wall means toward said distribution passage to interrupt the flow of breathable fluid therethrough and allow a fixed quantity of pressurized breathable fluid to flow into said plenum chamber, said second wall means responding to an inhalation pressure communicated from the nasal passages through said first conduit to said sensing chamber to allow the pressurized breathable fluid in said control chamber to flow through said relief passage into said relief chamber and permit said fixed quantity of pressurized breathable fluid to communicate to the nasal passages of the recipient through said second conduit to meet an inhalation demand.

2. The control means, as recited in claim 1 wherein said housing includes:

a fourth passageway for connecting said relief chamber with said third passageway to allow said breathable fluid in said relief chamber to be communicated to said recipient.

3. The control means, as recited in claim 2 further including:

venturi means in said fourth passageway for asperating the breathable fluid from the constant volume chamber to prevent a pressure build-up in the constant volume chamber during said inhalation.

4. The control means, as recited in claim 3, wherein said housing further includes:

an atmospheric chamber for allowing atmospheric air pressure to move on said first wall means away from said relief passage during inhalation demand and thereby allow said pressurized breathable fluid to flow into said relief chamber.

5. The control means, as recited in claim 4, wherein said second wall means includes:

a first diaphragm secured to said housing to separate said sensing chamber from said relief passage;

a second diaphragm secured to said housing to separate said atmospheric chamber from said relief passages and establish said relief chamber between said sensing chamber and said atmospheric chamber; and linkage means secured to said first and second diaphragm for establishing a constant volume area for said relief chamber.

6. The control means, as recited in claim 5, further includes:

cannula means for combining said first and second conduits into a single structure for insertion into the nasal passages of the recipient.

7. A control means for only permitting the communication of pressurized breathable fluid to a recipient during an inhalation period of a breathing cycle, comprising:

a housing having a plenum chamber, a distribution chamber, a control chamber, a relief chamber, a sensing chamber, a sensing port and an outlet port said plenum chamber being connected to a source of pressurized breathable fluid by a first passageway, said housing having a plurality of varied flow rate orifices adjacent said plenum chamber through which said pressurized breathable fluid is communicated from said source to the plenum chamber, said sensing chamber being connected to said sensing port by a second passageway, said distribution chamber being connected to said outlet port by a third passageway, said control chamber being connected to said first passageway upstream of said plurality of orifices by a control passage and to said relief chamber by a relief passage, said relief chamber including means for relieving pressure accumulated therein, said plenum chamber being connected to said distribution chamber by a distribution passage;

first conduit means for connecting said sensing port with the nasal passages of the recipient;

second conduit means for connecting said outlet port with the nasal passages of the recipient;

actuator means located in said first passageway for permitting said pressurized breathable fluid to flow from said storage container;

selector means located in said first passageway for only permitting communication of pressurized breathable fluid through one of said plurality of orifices corresponding to the metabolic needs of the recipient;

first wall means for separating said control chamber from said distribution chamber and for controlling flow of fluid through said distribution passage; and sensor means located in said sensing chamber and responsive to inhalation and exhalation pressure signals communicated through said first conduit from the nasal passages of the recipient to establish a cycle of operation, said sensor means preventing the flow of pressurized breathable fluid through said relief passage during communication of an exhalation pressure signal to allow the pressurized breathable fluid in the control passage to flow into the control chamber and move said first wall means and seal said distribution passage to permit a fixed volume of pressurized breathable fluid to be stored in said plenum chamber, said sensor means allowing the flow of pressurized breathable fluid through the relief passage from the control chamber into the relief chamber during communication of an inhalation pressure signal to permit the fixed volume of pressurized breathable fluid to flow from the plenum chamber and into the distribution chamber for transmission to the recipient through the second conduit for the duration of the inhalation pressure signal.

8. The control means, as recited in claim 7, wherein said sensor means includes:

a first diaphragm for separating said sensing chamber from said relief chamber to prevent the pressurized breathable fluid flowing from said relief passage from effecting said inhalation pressure signal.

9. The control means, as recited in claim 8, wherein said sensor means further includes:

a second diaphragm for separating said relief passage from an atmospheric port; and strut means for connecting said first diaphragm with second diaphragm to establish a constant volume for said relief chamber.

10. The control means, as recited in claim 9, wherein said housing further includes:

a fourth passageway for connecting said relief chamber with said third passageway to provide a flow path for communicating the pressurized breathable fluid in said relief chamber to the recipient.

11. The control means, as recited in claim 10, further including:

check valve means located in said fourth passageway for preventing communication between said relief chamber and said third passageway during the development of the exhalation pressure signal in the breathing cycle.

12. The control means, as recited in claim 7, further comprising:

regulator means located in said passageway for maintaining the pressure of the breathable fluid at a substantially uniform level.

13. The control means, as recited in claim 7, wherein said regulator means includes:

second wall means for separating a first cavity in the first passageway into a flow-through-chamber and an atmosphere chamber, said flow-through-chamber having an entrance port connected to the first passageway, a first exit port connected to said plurality of orifices and a second exit port connected to said control passage;

spring means connected to the housing for urging the second wall means toward the flow-through-chamber; and poppet means adjacent the entrance port and responsive to a predetermined movement of said wall means for allowing said breathable fluid to flow from the storage container into the flow-through-chamber when the force of the spring means and air at atmospheric pressure exceed the force of the pressurized breathable fluid in the flow-through chamber.

* * * * *